US010603227B2

(12) United States Patent
Köktürk et al.

(10) Patent No.: US 10,603,227 B2
(45) Date of Patent: Mar. 31, 2020

(54) DIAPER WITH TRANSVERSE BARRIERS

(71) Applicant: ONTEX BVBA, Buggenhout (BE)

(72) Inventors: Hayri Köktürk, Istanbul (TR); Gül Gürsoy, Istanbul (TR); Özgür Akyildiz, Lasne (BE); Ahmet Halilbeyoglu, Istanbul (TR); Pek Gökmen, Istanbul (TR); Hans-Joerg Hufnagel, Bonn (DE); Helen Assenheimer, Sinzheim (DE)

(73) Assignees: ONTEX BVBA, Buggenhout (BE); ONTEX GROUP NV, Erembodegem (BE)

( * ) Notice: Subject to any disclaimer, the term of this patent is extended or adjusted under 35 U.S.C. 154(b) by 0 days.

(21) Appl. No.: 16/313,123

(22) PCT Filed: Aug. 26, 2016

(86) PCT No.: PCT/EP2016/070210
§ 371 (c)(1),
(2) Date: Dec. 24, 2018

(87) PCT Pub. No.: WO2018/036639
PCT Pub. Date: Mar. 1, 2018

(65) Prior Publication Data
US 2019/0254886 A1 Aug. 22, 2019

(51) Int. Cl.
*A61F 13/494* (2006.01)
*A61F 13/49* (2006.01)
(Continued)

(52) U.S. Cl.
CPC .. *A61F 13/49017* (2013.01); *A61F 13/15804* (2013.01); *A61F 13/495* (2013.01);
(Continued)

(58) Field of Classification Search
CPC .......... A61F 13/49466; A61F 13/49473; A61F 2013/4948; A61F 2013/49486; A61F 2013/49493
See application file for complete search history.

(56) References Cited

U.S. PATENT DOCUMENTS

| 4,753,646 A | 6/1988 | Enloe |
| 4,808,177 A * | 2/1989 | DesMarais ........ A61F 13/49017 |
| | | 604/385.27 |

(Continued)

FOREIGN PATENT DOCUMENTS

| EP | 0998891 A2 | 5/2000 |
| EP | 1199058 A1 | 4/2002 |

(Continued)

OTHER PUBLICATIONS

European Search Opinion in European App. No. 17183302.3, dated Oct. 26, 2017.
(Continued)

*Primary Examiner* — Susan S Su
(74) *Attorney, Agent, or Firm* — Vivicar Law, PLLC (57) ABSTRACT

The current invention concerns an absorbent hygiene article suitable to be worn around the waist of a wearer, such as a diaper, diaper pants or incontinence diaper, the article comprising a leakage barrier comprising a pair of leg cuffs arranged longitudinally on the body-facing side of the article from the front region to the back region across the crotch region, a first leg cuff of said pair of leg cuffs being arranged near a first leg hole defining edge of the article and a second leg cuff of said pair of leg cuffs being arranged near a second leg hole defining edge of the article and a front barrier and/or a back barrier, wherein the front barrier and/or the back barrier comprises a liquid-impermeable nonwoven sheet comprising a weight of at most 18 gsm and in that the elastic members of the leg cuffs do not overlap with the front barrier
(Continued)

and/or the back barrier. The present invention also pertains to methods and apparatuses for manufacturing the article and the leakage barrier.

17 Claims, 5 Drawing Sheets (51) Int. Cl.
*A61F 13/495* (2006.01)
*A61F 13/15* (2006.01)

(52) U.S. Cl.
CPC .. *A61F 13/49058* (2013.01); *A61F 13/49413* (2013.01); *A61F 13/49426* (2013.01); *A61F 13/49473* (2013.01); *A61F 13/4942* (2013.01); *A61F 13/4946* (2013.01); *A61F 13/49466* (2013.01); *A61F 2013/4951* (2013.01); *A61F 2013/4956* (2013.01); *A61F 2013/49092* (2013.01)

(56) References Cited

U.S. PATENT DOCUMENTS

| | | | |
|---|---|---|---|
| 4,938,755 A * | 7/1990 | Foreman | A61F 5/4401 604/385.27 |
| 5,366,453 A | 11/1994 | Zehner et al. | |
| 5,827,259 A * | 10/1998 | Laux | A61F 13/49011 604/385.29 |
| 5,935,118 A | 8/1999 | Gryskiewicz et al. | |
| 6,132,410 A * | 10/2000 | Van Gompel | A61F 13/49017 604/358 |
| 6,217,563 B1 * | 4/2001 | Van Gompel | A61F 13/49017 604/378 |
| 6,336,922 B1 * | 1/2002 | VanGompel | A61F 13/49011 604/385.29 |
| 6,794,557 B1 | 9/2004 | Klemp et al. | |
| 7,785,309 B2 * | 8/2010 | Van Gompel | A61F 13/4942 604/385.01 |
| 10,010,458 B2 * | 7/2018 | Barnes | A61F 13/49012 |
| 10,159,610 B2 * | 12/2018 | Barnes | A61F 13/49011 |
| 2007/0197987 A1 | 8/2007 | Tsang et al. | |
| 2010/0305533 A1 * | 12/2010 | Ashton | A61F 13/4946 604/367 |
| 2016/0270978 A1 * | 9/2016 | Raycheck | A61F 13/55105 |
| 2017/0000658 A1 * | 1/2017 | Chatterjee | A61F 13/4902 |
| 2017/0246044 A1 * | 8/2017 | Ludwig | A61F 13/475 |
| 2017/0333262 A1 * | 11/2017 | Chatterjee | A61F 13/15 |

FOREIGN PATENT DOCUMENTS

| | | |
|---|---|---|
| EP | 1224922 A2 | 7/2002 |
| GB | 2297683 A | 8/1996 |
| WO | 9607382 A2 | 3/1996 |
| WO | 9715260 A1 | 5/1997 |
| WO | 2010109866 A1 | 9/2010 |

OTHER PUBLICATIONS

International Search Report and Written Opinion for PCT/EP2016/070210, dated Apr. 26, 2017.

* cited by examiner

DIAPER WITH TRANSVERSE BARRIERS

CROSS-REFERENCE TO RELATED APPLICATIONS

This application is the national stage application of corresponding international application number PCT/EP2016/070210, filed Aug. 26, 2016, which is hereby incorporated by reference in its entirety.

TECHNICAL FIELD

The invention pertains to the technical field of absorbent hygiene products. In particular, the present invention relates to an absorbent article for absorbing body fluids and exudates, such as urine and fecal material. More particularly, the present invention relates to absorbent garments which can be worn around the waist of a user, such as disposable diapers or diaper pants, which are configured to collect and contain fecal material and avoid leakage.

BACKGROUND

In absorbent garments (diapers, diaper pants and incontinence diapers), bodily exudates are absorbed by an absorbent core positioned in a crotch region of the garment. Typically, the exposure of the core to exudates is unevenly distributed in time, i.e. insults of e.g. urine or faces occur within a short time interval on separate occasions. Hereby, it can happen that the absorbent core is not capable of absorbing all exudates essentially within the short time interval of the insult. Consequently, exudates can flow or distribute over the absorbent core towards edges of the garment, leading to possible leakages. In order to resolve this, barriers are provided on the body-facing side of the garment which attempt to contain the exudates within the boundaries of the garment.

Many absorbent garments thereto comprise leg barriers which are provided around and/or near the leg holes of the garment, having as main function to keep the sides of the garment against the wearer's legs during use to contain the exudates. Alternatively or in addition, many absorbent garments may comprise leg cuffs which are provided longitudinally on the body-facing side of the garment, near the transverse edges of the garment, and which are configured to be elevated over the absorbent core and/or topsheet of the garment such that a space is obtained between the wearer and the topsheet of the garment at the crotch region. This space allows temporary storage of the exudates and prevents at least partially that exudates are pushed outwards due to the pressure exerted thereon by the wearer's buttocks and the garment. In many cases, both leg barriers and leg cuffs are provided on the absorbent garment to provide a double protection against leakages.

European patent application EP 1 199 058 A1 discloses a disposable wearing article which includes a substantially liquid-impervious leak-barrier cuff which has a fixed end portion lying in the vicinity of a longitudinal end portion of an article, a free end portion extending from the fixed end portion toward a crotch region and fixed lateral end portions lying on transversely opposite side edge portions of the article. The free end portion is normally biased by an elastic member attached to the free end portion to rise over a topsheet and being locally bonded to the article in retaining zones.

European patent application EP 2 410 966 A1 discloses an absorbent article which is provided with a waist-cuff to prevent body waste from leaking beyond a waist-opening. An elastic sheet is used for the waist-cuff to be held in contact with the wearer's skin even if the wearer moves. The waist-cuff and a chassis may be joined to each other so as to be separated from each other in the vicinity of an absorbent structure to assure that fitness of the waist-cuff to the wearer's skin is not significantly affected by movement of the wearer and, at the same time, to assure that leg-cuffs can rise without being collapsed by the waist-cuff. The ends of the leg-cuffs are interleaved between the waist-cuff and the chassis to prevent body waste from leaking through a clearance which would otherwise be defined between the leg-cuffs and the waist-cuff.

European patent application EP 0 779 802 A2 discloses a disposable diaper having a waist pocket cuff is disclosed. The pocket cuff has an open edge having an apex. The open edge extends between ends joined to the distal edges of barrier cuffs. The open edge is elastically biased to form the open edge apex along the longitudinal centerline of the disposable diaper.

There remains a need in the art for a disposable absorbent hygiene article, suitable to be worn around the waist of a wearer, with improved leakage barrier at the sides of the article, as well as at the waist front and/or waist back of the article.

There also remains a need in the art for a disposable absorbent hygiene article, suitable to be worn around the waist of a wearer, with a leakage barrier at the sides of the article, as well as at the waist front and/or waist back of the article, which can be easily constructed with less material and less production steps.

There also remains a need in the art for methods and apparatuses for manufacturing said leakage barrier and said hygiene article. The present invention aims to resolve at least some of the problems mentioned above.

SUMMARY OF THE INVENTION

The present invention provides an absorbent hygiene product, suitable to be worn around the lower torso of a wearer, such as a disposable baby diaper, baby diaper pants, incontinence diaper, incontinence diaper pants, according to claim 1.

The product of the present invention overcomes the problems of prior art products, in particular with the leakage barrier, and in particular the front barrier and/or back barrier comprises, and preferably essentially consists only of, a nonwoven liquid-impermeable sheet of low weight, in particular of at most 18 gsm (gram per squared meter), preferably at most 17 gsm, more preferably at most 16 gsm, yet more preferably at most 15 gsm, still more preferably at most 14 gsm, even more preferably at most 13 gsm, most preferably at most 12 gsm, such as 11, 10, 9, 8, 7, 6 gsm or less.

The applicant has noted that simply reducing the weight of the front barrier and/or back barrier to at most 18 gsm, can lead to problems of tearing and of reduced capability of the front and/or back barrier of being lifted over the topsheet. The applicant has found that the reduced capability of being lifted of the front/back barrier is primarily due to wrinkling of the low-weight barrier's side edges, this wrinkling also being partially responsible for the tearing of the low-weight barrier. The applicant has therefore found that it is necessary to ensure that front barrier and/or back barrier is not attached to the leg cuffs at the position of the leg cuff elastics, i.e. the elastic members in the leg cuffs which ensure that the leg cuff can be lifted over the top sheet. Hence the problem of tearing and of reduced lifting of the low-weight front and/or back barrier is solved by the leg cuff elastic members not overlapping the front barrier and/or the back barrier.

Moreover, in hygiene articles whereby the front/back barrier are attached to the leg cuffs, it seemed to be necessary to attach the front/back barrier at the region of the leg elastics to ensure that the front/back barrier could be lifted. In the present invention, the reduced weight of the front/back barrier nonwoven sheet allows the front/back barrier to be lifted even if it is attached to a part of the leg cuffs which does not comprise leg cuff elastics. Hence, the features of providing a low-weight front barrier and/or back barrier and of the leg cuff elastic members not overlapping the front barrier and/or back barrier cooperate synergistically to achieve the desired effect of forming a pocket-shaped leakage barrier which is easier and cheaper to produce than prior art pocket barriers.

In a further aspect, the present invention provides a method for manufacturing an absorbent hygiene product as further specified in the claims, said absorbent hygiene product being a product according to claim 1.

In particular, the present invention relates to a method for manufacturing an absorbent hygiene article according to the present invention, the method comprising the steps of:

(1) providing an article preform comprising a front region, a back region and a crotch region located longitudinally in between the front region and the back region, the article preform further comprising a liquid impermeable backsheet on a garment-facing side of the article, a liquid permeable topsheet on the body-facing side of the article and an absorbent core therebetween, the absorbent core substantially located in the crotch region;

(2) providing a leakage barrier comprising a pair of leg cuffs, each of the leg cuffs comprising a front end edge, a back end edge, a longitudinal proximal edge and a longitudinal distal edge,
wherein each of the leg cuffs comprises one or more elastic members such as elastic strands, the elastic members being arranged longitudinally near the distal edge of the leg cuff,
wherein the leakage barrier further comprises:
a front barrier comprising a first front barrier edge attached to the first leg cuff near the distal edge of the first leg cuff, the front barrier comprising a second front barrier edge attached to the second leg cuff near the distal edge of the second leg cuff, the front barrier comprising a front barrier waist edge and the front barrier comprising a front barrier internal edge; and/or
a back barrier comprising a first back barrier edge attached to the first leg cuff near the distal edge of the first leg cuff, the back barrier comprising a second back barrier edge attached to the second leg cuff near the distal edge of the second leg cuff, the back barrier comprising a back barrier waist edge and the back barrier comprising a back barrier internal edge, (3) attaching the leakage barrier to the body-facing side of the article preform,
wherein the front barrier and/or the back barrier comprises a liquid-impermeable nonwoven sheet comprising a weight of at most 18 gsm and in that the elastic members of the leg cuffs do not overlap with the front barrier and/or the back barrier.

Preferably, the step (2) of providing the leakage barrier comprises attaching the first front barrier edge to the first leg cuff near the distal edge of the first leg cuff and attaching the second front barrier edge to the second leg cuff near the distal edge of the second leg cuff, and/or attaching the first back barrier edge to the first leg cuff near the distal edge of the first leg cuff and attaching the second back barrier edge to the second leg cuff near the distal edge of the second leg cuff, most preferably by heat-sealing.

To obtain the hygiene article, the leakage barrier is attached to the body-facing side of the article preform such that the pair of leg cuffs are arranged longitudinally on the body-facing side of the article preform, whereby a first leg cuff of said pair of leg cuffs is arranged such that its proximal edge is or will be attached longitudinally near a first leg hole defining edge of the hygiene article and a second leg cuff of said pair of leg cuffs is arranged such that its proximal edge is or will be attached longitudinally near a second leg hole defining edge of the hygiene article. Hereby, the front end edge of each leg cuff is attached in the front region of the article preform and the back end edge of each leg cuff is attached in the back region of the article preform, while the longitudinal distal edge of each leg cuff is substantially unattached.

If a front barrier is provided, it will be attached to the front region of the article preform, whereby the front barrier waist edge will be attached to a topsheet of the article preform such that it is or will be located near a front waist edge of the hygiene article. The front barrier internal edge will be substantially unattached. Analogously, if a back barrier is provided, it will be attached to the back region of the article preform, whereby the back barrier waist edge will be attached to a topsheet of the article preform such that it is or will be located near a back waist edge of the hygiene article. The back barrier internal edge will be substantially unattached.

In a possible embodiment, the front and/or back barrier can comprise (or consist entirely of) nonwovens, for instance super absorbent-nonwovens (SA), super absorbent particle-nonwoven (SAP) or super absorbent fiber-nonwoven (SAF). The latter, SAF-nonwoven, can be a nonwoven substantially made from super absorbent fibers, or super absorbent fibers applied like a nonwoven. By using SAF, this allows processing of the absorbent material as a nonwoven as well, instead of only as (granular) particles as with SAP. SAF can be used in the core of the front and/or back barrier, but also in other parts of the front and/or back barrier, such as (parts of) sheets holding the absorbent core. Furthermore, the SAF can be provided in a fibrous form (laminate) on its own (possibly supplemented with other fibers), or can be integrated within a different nonwoven fabric or in a spun yarn as a mixture of several substrates. This has its advantages in processability, combined with the excellent absorbency characteristics of the SAF. The front and/or back barrier can have a body-facing sheet comprising the SAF, preferably in a laminate form (or mixed form) which will contact the skin of the wear, with a non-absorbent nonwoven facing outwardly. Alternatively, the body-facing sheet can be the non-absorbent nonwoven, while the outward-facing sheet can comprise the SAF as mentioned. Even further, both sides may comprise the SAF. These measures can improve the barrier function of the front and/or back barrier.

The present invention further concerns the leakage barrier as disclosed here above, in the claims and further below, as well as a method and apparatus for manufacturing such a leakage barrier.

DETAILED DESCRIPTION OF THE INVENTION

The present invention concerns an absorbent hygiene article comprising a leakage barrier with a back barrier and/or a front barrier, a manufacturing method for such hygiene article, a leakage barrier with a back barrier and/or a front barrier, a manufacturing method for such a leakage barrier, as well as an apparatus therefor.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like, as well as surgical bandages and sponges. Absorbent articles preferably comprise a longitudinal axis and a transversal axis perpendicular to said longitudinal axis. The longitudinal axis is hereby conventionally chosen in the front-to-back direction of the article when referring to the article being worn, and the transversal axis is conventionally chosen in the left-to-right direction of the article when referring to the article being worn. Disposable absorbent articles can include a liquid pervious top sheet, a back sheet joined to the top sheet, and an absorbent core positioned and held between the top sheet and the back sheet. The top sheet is operatively permeable to the liquids that are intended to be held or stored by the absorbent article, and the back sheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface.

An absorbent article, such as a diaper, comprises a front waistband region, a back waistband region, an intermediate crotch region which interconnects the front and rear waistband regions. When used herein, reference to a "front" portion refers to that part of the diaper which is generally located on the front of a wearer when in use. Reference to the "rear" portion refers to the portion of the diaper generally located at the rear of the wearer when in use, and reference to the "crotch" portion refers to that portion which is generally located between the legs of a wearer when in use. The crotch region is an area where repeated fluid surge typically occurs.

Preferably, the hygiene article of the present invention comprises a liquid permeable "top sheet", a liquid impermeable "back sheet", and an "absorbent medium" disposed between the top sheet and the back sheet. The top sheet, back sheet and the absorbent medium could be made from any suitable material known to the person skilled in the art. The top sheet is generally located at or near the bodyside surface of the article, while the back sheet is generally located at or near the garment-side surface of the article. Optionally, the article may comprise one or more separate layers which are in addition to the back sheet and are interposed between the back sheet and the absorbent medium. Top sheet and back sheet are connected or otherwise associated together in an operable manner.

The "absorbent medium" or "absorbent core" or "absorbent body" is the absorbent structure disposed between the top sheet and the back sheet of the absorbent article in at least the crotch region of the absorbent article and is capable of absorbing and retaining liquid body exudates. The size and the absorbent capacity of the absorbent medium should be compatible with the size of the intended wearer and the liquid loading imparted by the intended use of the absorbent article. Further, the size and the absorbent capacity of the absorbent medium can be varied to accommodate wearers ranging from infants through adults. It may be manufactured in a wide variety of shapes (for example, rectangular, trapezoidal, T-shape, I-shape, hourglass shape, etc.) and from a wide variety of materials. Examples of commonly occurring absorbent materials are cellulosic fluff pulp, tissue layers, highly absorbent polymers (so called superabsorbent polymer particles (SAP)), absorbent foam materials, absorbent nonwoven materials or the like. It is common to combine cellulosic fluff pulp with superabsorbent polymers in an absorbent material.

The term "adhesive" or "glue" as used herein is intended to refer to any suitable hot melt, water or solvent borne adhesive that can be applied to a surface of a film layer in the required pattern or network of adhesive areas to form the film-nonwoven laminate of the present invention. Accordingly, suitable adhesives include conventional hot melt adhesives, pressure-sensitive adhesives and reactive adhesives (i.e., polyurethane).

As used herein, the term "adhesive bonding" or "gluing" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

The terms "back section", "back region" and "rear back section" and "rear back region" are used herein as synonyms and refer to the area of the absorbent article which is contact with the back of the wearer when the absorbent article is worn.

The term "back sheet" refers to a material forming the outer cover of the absorbent article. The back sheet prevents the exudates contained in the absorbent structure from wetting articles such as bedsheets and overgarments which contact the disposable absorbent article. The back sheet may be a unitary layer of material or may be a composite layer composed of multiple components assembled side-by-side or laminated. The back sheet may be the same or different in different parts of the absorbent article. At least in the area of the absorbent medium the back sheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The back sheet material may be breathable so as to allow vapour to escape from the absorbent material, while still preventing liquids from passing there through. Examples of breathable back sheet materials are porous polymeric films, nonwoven laminates of spunbond and meltblown layers and laminates of porous polymeric films and nonwoven materials.

The terms "belly section", "front section", "front region", "front belly section" and "front belly region" are used herein as synonyms and refer to the area of the absorbent article which is in contact with the belly of the wearer when the absorbent article is worn.

As used herein, the "body-facing" or "bodyside" surface means that surface of the article or component which is intended to be disposed toward or placed adjacent to the body of the wearer during ordinary use, while the "outward", "outward-facing", "garment-facing" or "garment-side" surface is on the opposite side, and is intended to be disposed to face away from the wearer's body during ordinary use. Such outward surface may be arranged to face toward or placed adjacent to the wearer's undergarments when the absorbent article is worn.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

The hygiene article of the present invention comprises "leg cuffs", which is used synonymously to "containment flaps" or "barrier cuffs". The leg cuffs are generally thought to be particularly well suited for the containment of fecal matter and to prevent the lateral flow of liquid waste until such time as the liquid waste can be absorbed by the absorbent article. Many constructions of leg cuffs are known. Such leg cuffs generally comprise a proximal edge, intended to be attached to the absorbent article, and an opposite distal edge which is generally not attached to the absorbent article along at least a portion of its length. An elastic member is generally located adjacent the distal edge to assist in maintaining the leg cuff in an upright condition and in maintaining a sealing relationship between the distal edge of the leg cuff and the body of a wearer during use. The elastic member is generally located between two layers of material so that the elastic does not come into contact with the body of a wearer. The leg cuffs may be manufactured from a wide variety of materials such as polypropylene, polyester, rayon, nylon, foams, plastic films, formed films, and elastic foams. A number of manufacturing techniques may be used to manufacture the leg cuffs. For example, the leg cuffs may be woven, non-woven, spunbonded, carded, cast, blown or the like.

"Elongation" means the ratio of the extension of a material to the length of the material prior to the extension (expressed in percent), as represented by the following: "Extension" means the change in length of a material due to stretching (expressed in units of length).

The term "finished" or "final", when used with reference to a product, means that the product has been suitably manufactured for its intended purpose.

As used herein, the term "garment" means any type of apparel which may be worn. This includes diapers, training pants, incontinence products, surgical gowns, industrial workwear and coveralls, undergarments, pants, shirts, jackets and the like.

As used herein, the term "impermeable" generally refers to articles and/or elements that are substantially not penetrated by aqueous fluid through the entire thickness thereof under a pressure of 1.0 kPa or less. Preferably, the impermeable article or element is not penetrated by aqueous fluid under pressures of 3.4 kPa or less. More preferably, the impermeable article or element is not penetrated by fluid under pressures of 6.8 kPa or less. An article or element that is not impermeable is permeable. "Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. The elements can be joined directly together, or have one or more elements interposed between them, all of which are connected together.

The term "laid-flat state", "stretched-out state" or "extended state" is intended to refer to the article when it is flattened into a plane or is substantially flattened into a plane and is used in contrast to when the article otherwise positioned, such as when the article is folded or shaped in or for use by a wearer.

The crotch portion of the hygiene article according to the present invention comprises opposite longitudinal side portions which comprise a pair of elasticized, longitudinally-extending "leg cuffs". The leg cuffs are generally adapted to fit about the legs of a wearer when in use and serve as a mechanical barrier to the lateral flow of body exudates. Leg cuffs are elasticized by leg elastics. The hygiene article further preferably comprises a front waist elastic and/or a rear waist elastic. Materials suitable for use in forming leg elastics are known to those skilled in the art. Exemplary of such materials are strands or ribbons of a polymeric, elastomeric material which are adhered to the diaper at the leg cuff while in a stretched position, or which are attached to the diaper while the diaper is pleated, such that elastic constrictive forces are imparted to the leg cuff. Examples of suitable elastomer materials that can be used include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

The term "top sheet" refers to a liquid permeable material sheet forming the inner cover of the absorbent article and which in use is placed in direct contact with the skin of the wearer. The top sheet is typically employed to help isolate the wearer's skin from liquids held in the absorbent structure. The top sheet can comprise a nonwoven material, e.g. spunbond, meltblown, carded, hydro-entangled, wetlaid etc. The top sheet material may further be composed of two fibers, which may be bonded to each other in a bonding pattern. Further examples of top sheet materials are porous foams, apertured plastic films, laminates of nonwoven materials and apertured plastic films etc. The inner coversheet may further be different in different parts of the absorbent article. The top sheet fabrics may be composed of a substantially hydrophobic material, and the hydrophobic material may optionally be treated with a surfactant or otherwise processed to impart a desired level of wettability and hydrophilicity.

In a first aspect, the present invention provides an absorbent hygiene article, suitable to be worn around the lower torso of a wearer. An embodiment of such a hygiene article is shown in FIG. 1.

Figure 1:
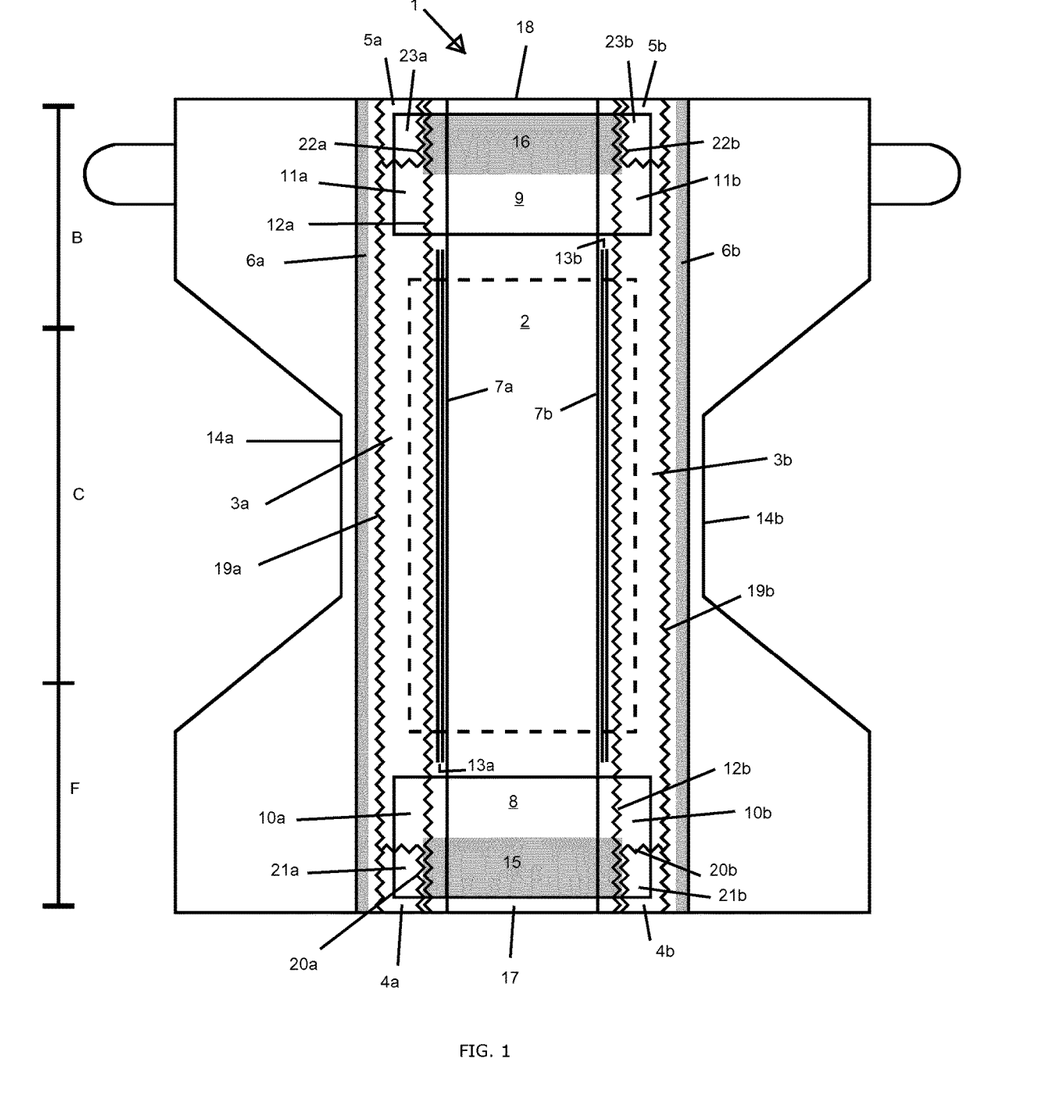
FIG. 1 shows an absorbent hygiene article according to the present invention.

FIG. 1 shows an absorbent hygiene article (1) comprising a front region (F), a back region (B) and a crotch region (C) therebetween. The hygiene article comprises an absorbent core (2) indicated by the dashed lines and located mainly in the crotch region (C). In preferred embodiments, the absorbent core (2) is located in between a topsheet at a body-facing side of the hygiene article and a backsheet at a garment-facing side of the hygiene article.

The article further comprises a pair of leg cuffs (3a, 3b), a first leg cuff (3a) and a second leg cuff (3b). Each of the leg cuffs comprises a front end edge (4a, 4b), a back end edge (5a, 5b), a longitudinal proximal edge (6a, 6b) and a longitudinal distal edge (7a, 7b). The leg cuffs (3a, 3b) are provided with elastic members (13a, 13b) which are wrapped within a fold of the leg cuffs (3a, 3b) near the distal edges (7a, 7b).

The article also comprises a front barrier (8) in the front region (F) and a back barrier (9) in the back region (B). The front barrier (8) comprises a first front barrier edge (10a) attached to the first leg cuff (3a) near the distal edge (7a) of the first leg cuff (3a) and a second front barrier edge (10b) attached to the second leg cuff (3b) near the distal edge (7b) of the second leg cuff (3b). The back barrier (9) comprises a first back barrier edge (11a) attached to the first leg cuff (3a) near the distal edge (7a) of the first leg cuff (3a) and a second back barrier edge (10b) attached to the second leg cuff (3b) near the distal edge (7b) of the second leg cuff (3b). The attachment of the front barrier (8) and the back barrier (9) to the leg cuffs (3a, 3b) is done along longitudinal attachment paths (12a, 12b), preferably by heat-sealing. The attachment paths (12a, 12b) hereby preferably extend along the full length of the leg cuffs (3a, 3b), hereby enclosing elastic members (13a, 13b) between a distal edge (7a, 7b) and an attachment path (12a, 12b), thereby preferably providing additional containment of the elastic members within the fold of the leg cuff.

The leakage barrier is attached to the body-facing side of an article preform. Hereby each of the leg cuffs (3a, 3b) is attached longitudinally near a leg-hole defining edge (14a, 14b) of the article or article preform. The leakage barrier is preferably attached by gluing and/or by heat-sealing to the article preform. The embodiment of FIG. 1 shows a preferred attachment comprising, wherein zig-zag lines refer to heat-sealing attachments and grey areas refer to gluing zones of attachment:

gluing a front barrier waist edge (15) to the topsheet of the article near a front waist edge (17) of the article preform and gluing a back barrier waist edge (16) to the topsheet of the article preform near a back waist edge (18) of the article;

gluing the proximal edges (6a, 6b) of the leg cuffs along essentially the full length to the topsheet of the article preform;

heat-sealing the leg cuffs along a longitudinal path (19a, 19b) to the topsheet of the article preform, the longitudinal path located near a proximal edge of the leg cuffs;

heat-sealing the front barrier and each of the leg cuffs to the article preform along a first path and a second path, the first path (20a) attaching a part of the front barrier waist edge (15) and a part of a first front barrier edge (21a) together with a front edge (4a) of the first leg cuff (3a) to the article preform and the second path (20b) attaching a part of the front barrier waist edge (15) and a part of a second front barrier edge (21b) together with a front edge (4b) of the second leg cuff (3b) to the article preform, and heat-sealing the back barrier and each of the leg cuffs to the article preform along a third path and a fourth path, the third path (22a) attaching a part of the back barrier waist edge (16) and a part of a first back barrier edge (23a) together with a back edge (5a) of the first leg cuff (3a) to the article preform and the fourth path (22b) attaching a part of the back barrier waist edge (16) and a part of a second back barrier edge (23b) together with a back edge (5b) of the second leg cuff (3b) to the article preform.

In a preferred embodiment, the front barrier and/or the back barrier are attached in between the leg cuffs and the topsheet of the article preform for an improved containment of fluids by the front barrier and/or back barrier.

In a preferred embodiment, the front barrier is glued to the topsheet over a zone which extends from the front barrier waist edge to over at least 5%, preferably at least 10%, more preferably at least 20%, such as 25%, 30%, 35%, 40%, 45% or, most preferably about 50%, or any value therebetween, of the length of the front barrier, the length being measured along the longitudinal direction. In a preferred embodiment, the back barrier is glued to the topsheet over a zone which extends from the back barrier waist edge to over at least 5%, preferably at least 10%, more preferably at least 20%, such as 25%, 30%, 35%, 40%, 45% or, most preferably about 50%, or any value therebetween, of the length of the back barrier, the length being measured along the longitudinal direction.

In a preferred embodiment, the front barrier is heat-sealed to the leg cuffs over a distance which extends from the front barrier internal edge to over at least 5%, preferably at least 10%, more preferably at least 20%, such as 25%, 30%, 35%, 40%, 45% or, most preferably about 50%, or any value therebetween, of the length of the front barrier, the length being measured along the longitudinal direction. In a preferred embodiment, the back barrier is heat-sealed to the leg cuffs over a distance which extends from the back barrier internal edge to over at least 5%, preferably at least 10%, more preferably at least 20%, such as 25%, 30%, 35%, 40%, 45% or, most preferably about 50%, or any value therebetween, of the length of the back barrier, the length being measured along the longitudinal direction.

In a preferred embodiment, the heat-sealing attachments of the front barrier and/or the back barrier with the leg cuffs to the topsheet of the article preform are located on top of or essentially bordering a region of attachment by gluing which attaches the front barrier waist edge and/or the back barrier waist edge to the article preform. This ensures that essentially no gap is present for fluids at the front waist edge and/or the back waist edge, and thus ensures a better containment of the pocket cuff which is created when the leakage barrier is attached to the article preform.

In a preferred embodiment, front barrier and/or the back barrier are attached to the topsheet along zones of attachment, such as zones of glue near the front barrier waist edge (15) or back barrier waist edge (16) or zones of heat-sealing such as along the paths (20a, 20b, 22a, 22b), these zones of attachment preferably not overlapping the absorbent core (2) to ensure an optimal use of the absorbent core (2) and to ensure that the zones of attachment are not exposed to moisture for an extended period which could compromise the attachment of the leakage barrier. Note that the attachments typically can withstand temporary exposure to moisture and fluids, but that essentially direct contact of possibly several hours with an absorbent core which has taken up fluids and could be moist may compromise the attachments. Hence, in an even more preferred embodiment, the front barrier (8) and/or the back barrier (9) do not overlap the absorbent core (2) when the hygiene article is in a stretched-out state.

Figure 2:
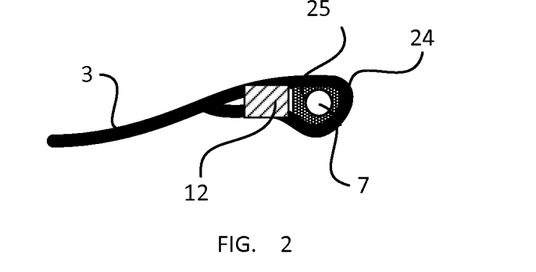
FIG. 2 shows an expanded cross-sectional view of a distal edge of a leg cuff of a leakage barrier and a hygiene article according to the present invention.

An expanded cross-sectional view of a distal edge of a leg cuff (3) is illustrated in FIG. 2. The leg cuff (3) comprises a fold (24) at the distal edge, the fold enclosing an elastic member (7), in this case an elastic strand. The fold is closed primarily with a (longitudinally) applied (band of) glue strip (25) (which glue preferably substantially fills said fold), which can be applied to the elastic member (7) itself or to the material of the fold enclosing the elastic member (7) (or both). The fold is additionally closed by heat-sealing along a longitudinally applied attachment path (12), which can be the same heat-sealed attachment used for attaching the front barrier and/or the back barrier to the distal edge of the leg cuff (see e.g. (12a) and (12b) in FIG. 1), or this can be actuated in an earlier step in the process, for instance during an elastification process in which the elastic members are wrapped within the fold and said fold is closed (at least partially). The heat-sealing of this attachment path (12) is thus doubly advantageous as it encloses the elastic member in the fold (doubly so if the elastic member is also attached to the fold of the leg cuff through glue or similar methods), while also attaching the leg cuff to the front and/or back barrier.

The present invention also concerns a method for manufacturing the hygiene product as e.g. illustrated in FIG. 1. The method includes the steps of providing the components of the hygiene article, i.e. an article preform, two leg cuffs and a front barrier and/or a back barrier, an attaching the components to each other to obtain the hygiene article. The applicant has found that one method, as further specified in the claims, is particularly preferred, as it allows easy incorporation into or adaptation of existing methods and/or apparatuses for manufacturing disposable hygiene articles suitable to be worn around the waist. Hereby, the applicant has found that it is best to first ensure attachment between the leg cuffs and the front barrier and/or back barrier, thereby providing a leakage barrier with leg cuffs and front barrier and/or back barrier. In a further step, the leakage barrier can be attached to an article preform, preferably by gluing and/or heat-sealing.

Figure 5:
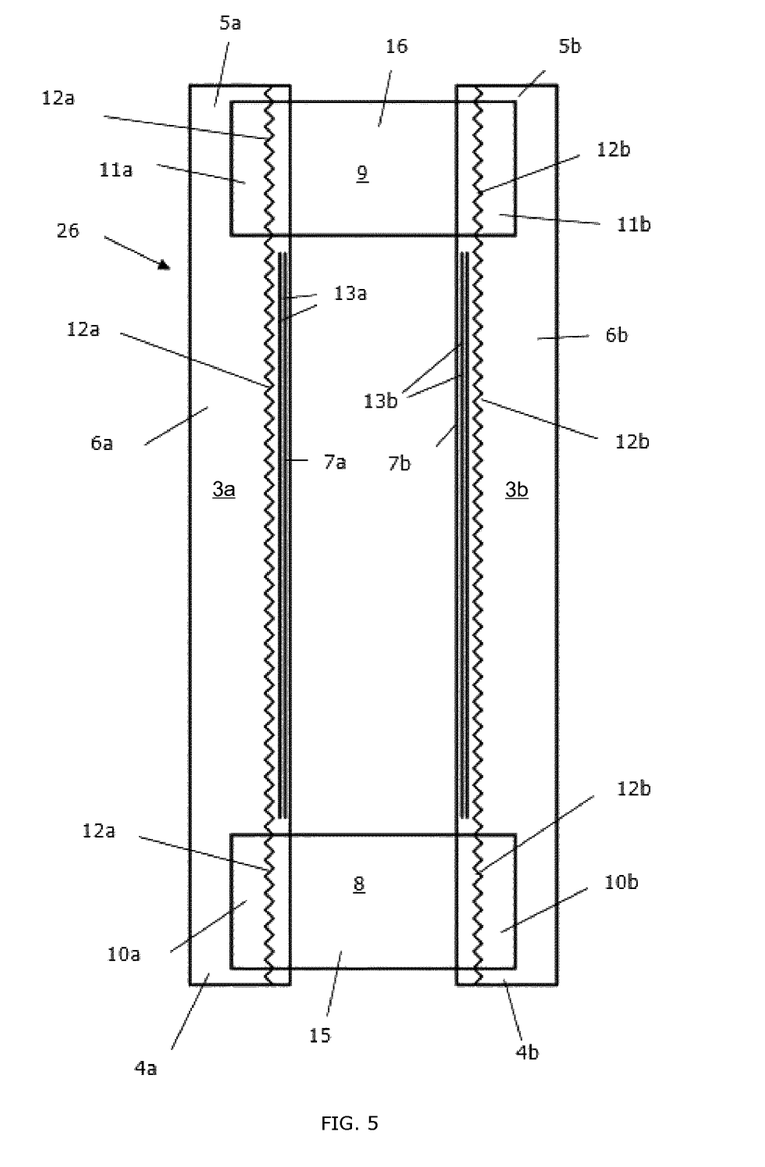
FIG. 5 illustrates an embodiment of a leakage barrier according to the present invention, which can be provided in the method of manufacturing a hygiene article according to the present invention.

FIG. 5 illustrates an embodiment of a leakage barrier (26) according to the present invention, which can be provided in the method of manufacturing a hygiene article. References in fig. are in correspondence with the references in FIG. 1.

Figure 3:
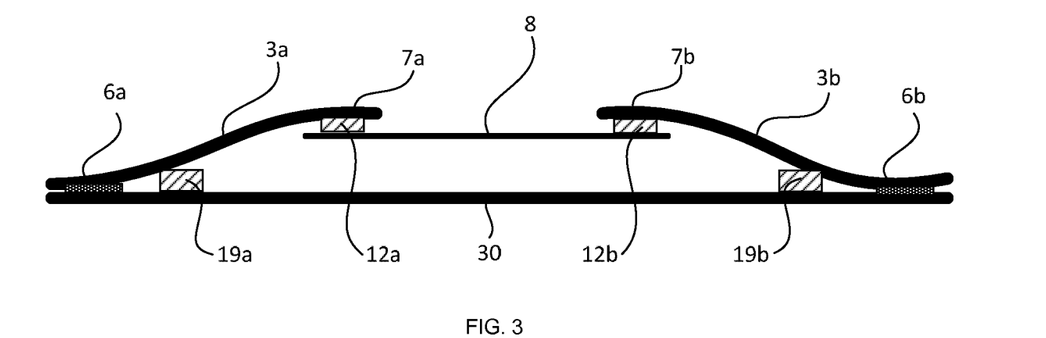
FIGS. 3 and 4 show cross-sectional views of a hygiene article according to the present invention.
Figure 4:
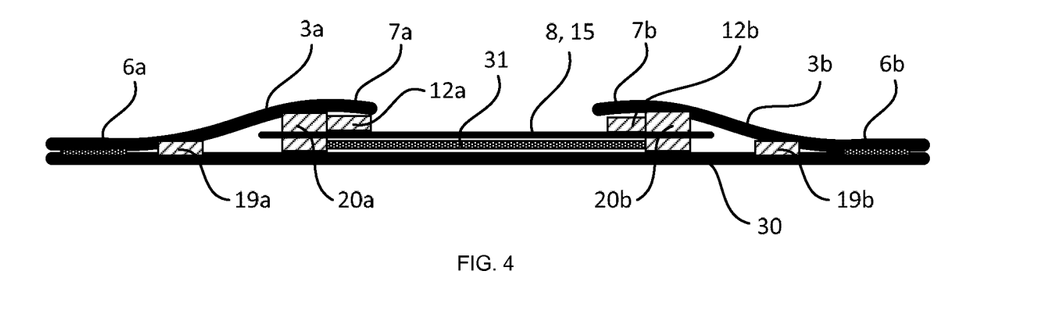

FIGS. 3 and 4 show cross-sectional views of a hygiene article according to the present invention. In FIG. 3, a transverse cross section is shown at the location of the front barrier near the front barrier internal edge. In FIG. 4, a transverse cross section is shown at the location of the front barrier near the front barrier waist edge. Shown are the leg cuffs (3a, 3b) which are attached to the front barrier (8) by heat sealing along longitudinal attachment paths (12a, 12b) near the distal edge (7a, 7b) of the leg cuffs. The cross sectional view of FIGS. 3 and 4 differ as they are taken at different positions along the longitudinal axis of the hygiene article. More in particular, FIG. 3 shows the cross section at the position of the front barrier near its internal edge, which is unattached to the topsheet (30), thereby allowing the front barrier to be spaced apart from the topsheet, whereas FIG. 4 shows the cross section at the position of the front barrier near its waist edge (15), which is attached to the topsheet (30) of the hygiene article or article preform. This difference is mainly reflected in the manner in which the leakage barrier is attached to the topsheet (30). Near the internal edge of the front barrier (FIG. 3), the leakage barrier is attached by gluing the proximal edges (6a, 6b), or a zone along or near (can be at a distance of 0.1 cm, 0.2 cm, 0.3 cm, 0.4 cm, 0.5 cm, 0.6 cm, 0.7 cm, 0.8 cm, 0.9 cm, 1 cm, 1.2 cm, 1.5 cm or more) to said proximal edges, of the leg cuffs (3a, 3b) to the topsheet (30) and by an adjacent heat-sealed attachment zone (19a, 19b). Near the waist edge (15) of the front barrier, the leakage barrier is additionally attached to the topsheet (30) by an essentially transversely applied gluing zone (31) which provides a strong attachment of the front barrier near the front waist edge, thereby blocking liquids to flow towards the front waist edge, and by a first attachment path (20a) and a second attachment path (20b) along which the front barrier and the leg cuffs are attached to the topsheet by heat-sealing. Hereby, the first path (20a) and second path (20b) are seen to connect to or essentially adjoin the gluing zone (31) to reduce the risk of leakage. The same principle preferably applies to the third and fourth attachment path (22a, 22b) on the opposite end of the hygiene article as well for attaching the back barrier, and the leg cuffs, to the topsheet.

In a preferred embodiment, the hygiene article of the present invention is a diaper, such as a baby diaper, a baby diaper pants, an incontinence diaper or an incontinence diaper pants. In a preferred embodiment, the diaper and/or the topsheet of the diaper comprises a width of between 15 and 55 cm, preferably between 16 and 40 cm, such as 17, 18, 19, 20, 21, 22, 23, 24, 25, 26, 27, 28, 29, 30, 31, 32, 33, 34, 35, 36, 37, 38, 39 cm or any value therebetween, the width of the diaper and/or topsheet being measured along a transverse direction perpendicular to the longitudinal direction. In a preferred embodiment, the front barrier and/or the back barrier comprises a width of between 6 and 25 cm, preferably between 6.5 and 20 cm, such as 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 cm or any value therebetween, the width of the front and/or back barrier being measured along a transverse direction perpendicular to the longitudinal direction. In a preferred embodiment, the front barrier comprises a length of between 2 and 15 cm, preferably between 3 and 12 cm, such as 3.5, 4, 4.5, 5, 5.5, 6, 6.5, 7, 7.5, 8, 8.5, 9, 9.5, 10, 10.5, 11, 11.5 cm or any value therebetween, the length being measured along the longitudinal direction. In a preferred embodiment, the back barrier comprises a length of between 2.5 and 17.5 cm, preferably between 3.5 and 15 cm, such as 4, 4.5, 5, 5.5, 6, 6.5, 7, 7.5, 8, 8.5, 9, 9.5, 10, 10.5, 11, 11.5, 12, 12.5, 13, 13.5, 14, 14.5 cm or any value therebetween, the length being measured along the longitudinal direction. Preferably the back barrier is longer than the front barrier.

Figure 6:
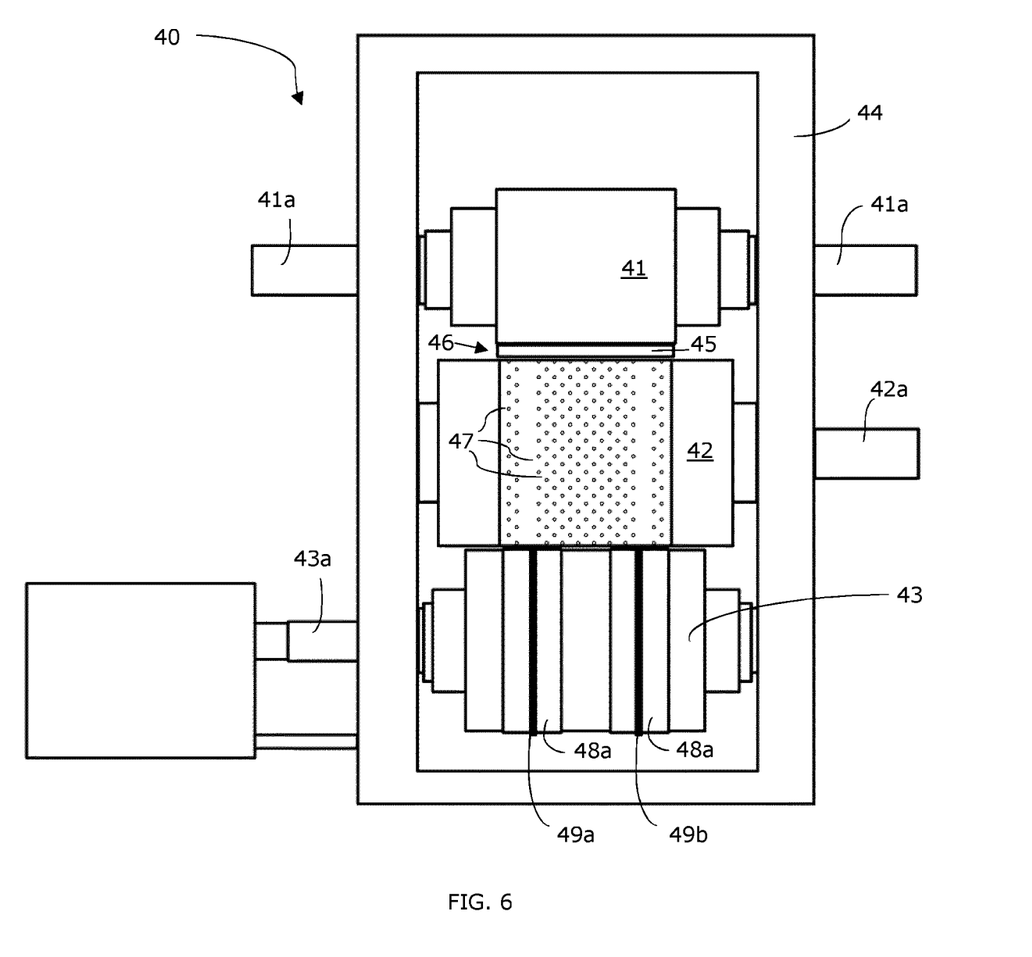
FIG. 6 shows an embodiment of an apparatus for manufacturing a leakage barrier according to the present invention.

FIG. 6 shows an embodiment of an apparatus for manufacturing a leakage barrier according to the present invention. The apparatus (40) comprises a cutting roller (41), an anvil roller (42) and an attachment roller (43), each rotatably mounted on a frame (44) by a cutting roller axis (41a), an anvil roller axis (42a) and an attachment roller axis (43a) respectively. The cutting roller and the anvil roller are configured to cut a front barrier and/or a back barrier from a sheet material by pressing a knife (45) of the cutting roller to a surface (46) of the anvil roller with the sheet material in between, the sheet material being a liquid-impermeable nonwoven sheet comprising a weight of at most 18 gsm.

The anvil roller (42) comprises holding means for holding the front barrier and/or the back barrier to the surface (46) of the anvil roller. In the shown embodiment, the holding means comprise a large number of orifices (47) on the surface (46) of the anvil roller (42). These orifices (47) are in fluid connection with suction means which create an underpressure at the position of the orifices such that the nonwoven for the front barrier and/or back barrier is sucked to the anvil's surface, and that the portions of nonwoven, which are cut by the cutting roller, also remain attached to the anvil's surface while being conveyed to the attachment roller.

In a preferred embodiment, the surface of the anvil roller comprises orifices which are preferably circular. Preferably, the anvil roller has a diameter of essentially between 20 and 500 mm, more preferably between 100 and 250 mm, yet more preferably between 130 and 200 mm, still more preferably between 150 and 170 mm, such as 151, 152, 153, 154, 155, 156, 157, 158, 159, 160, 161, 162, 163, 164, 165, 166, 167, 168, 169 mm or any value therebetween. Also preferably, the anvil roller has a circumference of essentially between 60 and 1600 mm, more preferably between 300 and 800 mm, yet more preferably between 390 and 640 mm, still more preferably between 450 and 544 mm, even more preferably between 590 and 610 mm, such as 491, 492, 493, 494, 495, 496, 497, 498, 499, 500, 501, 502, 503, 504, 505, 506, 507, 508, 509 mm or any value therebetween. Preferably the distance between orifices, from center to center, is between 2.5 and 30 mm, more preferably between 5 and 20 mm, yet more preferably between 8 and 15 mm, such as 9, 10, 11, 12, 13, 14 mm or any value therebetween. Preferably, the orifices comprise a diameter of between 1 and 5 mm, more preferably between 2 and 3 mm, such as 2.1, 2.2, 2.3, 2.4, 2.5, 2.6, 2.7, 2.8, 2.9 mm or any value therebetween. In a preferred embodiment, the anvil roller comprises a circumferential path along which between 20 and 100 orifices are positioned, more preferably between and 80, yet more preferably between 40 and 60, such as 41, 42, 43, 44, 45, 46, 47, 48, 49, 50, 51, 52, 53, 54, 55, 56, 57, 58, 59 orifices.

Material for the leg cuffs, typically in the form of two endless strips, preferably each already provided with elastic members at a pre-determined pitch, preferably nonwovens and/or hydrophobic material, is supplied in between the anvil roller (42) and the attachment roller (43) on two leg cuff zones (48a, 48b). The leg cuff zones (48a, 48b) can be provided with holding means for pulling on the leg cuff strips. Furthermore, the leg cuff zones (48a, 48b) are each provided with attachment means (49a, 49b), preferably heat-sealing attachment zones, which are configured to attach the leg cuffs, preferably along attachment paths (12a, 12b), to the front barrier and/or back barrier at predetermined positions, such that the front and/or back barrier do not overlap with the elastic members in the leg cuffs. Due to the position of said attachment means (49a, 49b) on the attachment roller (43), especially on the leg cuff zones (48a, 48b), these thereby (at least partly) provide the heat-sealing of the front and/or back barrier to the leg cuffs and furthermore the supplementary attachment (via heat-sealing) of the folds of the leg cuffs, thus allowing a more compact apparatus as the two processes can be combined in a single step. Hence, a leakage barrier according to the present invention is obtained and can be attached further down the process to an article preform.

In a preferred embodiment, the apparatus comprises a main encoder, preferably connected to a main shaft of the apparatus, for ensuring timely operation of the different parts of the apparatus, comprising any and any combination of the cutting roller, the anvil roller, the attachment roller, the supplying means for the nonwoven of the back barrier and/or front barrier, the supplying means for the leg cuff material, or other encoders for controlling parts of the apparatus.

In a preferred embodiment, the cutting roller is controlled by a cutting servo motor, which preferably comprises a multiturn absolute encoder, which keeps track of its position. Preferably, the multiturn absolute encoder for the cutting servo motor is controlled by the main encoder, thereby ensuring synchronous operation.

In a preferred embodiment, the anvil roller is controlled by an anvil servo motor, preferably comprising a multiturn absolute encoder. Preferably, the anvil roller and attachment roller are connected, e.g. by a system comprising one or more gears and/or a toothed belt, such that both anvil roller and attachment roller can be driven and controlled by the same servo motor. The anvil servo motor can be controlled by a main encoder.

In a preferred embodiment, the anvil servo motor and the cutting servo motor are configured such that the knife (46) of the cutting roller cuts the nonwoven of the back barrier and/or front barrier at a position on the anvil roller's surface where no orifices are located, i.e. the nonwoven is cut in between the orifices such that the knife always has a surface to press to.

Figure 7:
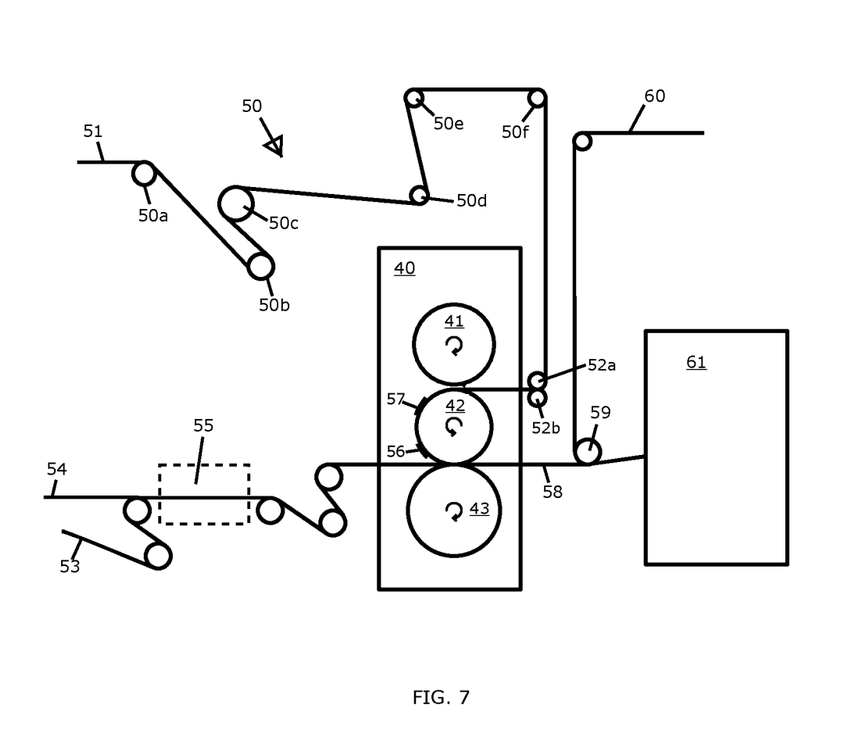
FIG. 7 illustrates the full process and apparatus for manufacturing the leakage barrier according to the present invention.

The full process and apparatus is further illustrated in FIG. 7. Herein, an endless nonwoven (51) for the front and/or back barrier is supplied by supplying means (50) comprising a set of guiding bars or rollers (50a, 50b, 50c, 50d, 50e, 50f) and a pair of pulling rollers (52a, 52b) to the leakage barrier manufacturing apparatus (40). The set of bars or rollers preferably comprises one or more rollers, e.g. rollers (50b) and (50c), whose rotational speed can be changed, thereby altering the supply speed of the nonwoven between the supply of nonwoven (51) and the pair of pulling rollers (52a, 52b). The rotational speed of the rollers (50b) and (50c) is preferably controlled in correspondence with the rotational speed of the pulling rollers (52a, 52b), e.g. by a single servo motor and a system of gears and/or timing belts, the single servo motor preferably controlled by a main encoder.

Two strips of leg cuffs (53) are provided separately from the barrier nonwoven (51). Elastic members (54), such as elastic strands are provided and attached to the leg cuff strips in a leg cuff elastification system (55). Preferably the elastic members are cut during the elastification process at predetermined intervals such that the elastified leg cuff strips comprise elastic strands at specific intervals. The elastified leg cuff strips are subsequently provided to the leakage barrier manufacturing apparatus (40).

The apparatus (40) cuts strips from the nonwoven (51) in between the cutting roller (41) and the anvil roller (42) to create front barriers and/or back barriers. Hereby, the cutting roller is preferably driven by a cutting servo motor, which is preferably controlled in such a manner that it cuts off a front barrier and/or a back barrier (56,57) at the moment which corresponds to the moment when said front barrier and/or back barrier needs to be attached to the leg cuff strips (53), taking into account the conveyance time by the anvil roller of the barrier, i.e. the time needed to convey the barrier from the position of cutting from the nonwoven to the position of attachment to the leg cuff strips. In a preferred embodiment, wherein the hygiene articles comprise both a front barrier and a back barrier, the cutting servo motor is configured to cut off a combined strip of front and back barrier, which is attached to the leg cuff strips, and which is cut in a later process in a front barrier and a back barrier of two subsequent hygiene articles, i.e. the barrier which is attached to the leg cuff strips by the attachment roller (43) overlaps the waist edges of subsequent hygiene articles and thus comprises the front barrier of a first hygiene article and the back barrier of a second hygiene article or vice versa.

The apparatus (40) provides a leakage barrier (58) comprising a pair of leg cuffs and a front barrier and/or a back barrier, in the form of subsequent leakage barriers whose leg cuffs are still attached at longitudinal ends, e.g. a front end edge (4a, 4b) of a leg cuff (3a, 3b) of a first leakage barrier is still attached to a back end edge (5a, 5b) of a leg cuff (3a, 3b) of a second leakage barrier. The leakage barrier (58) is subsequently combined, e.g. via a roller (59), with the topsheet of an article preform (60) in a subsequent attachment system (61), the topsheet preferably provided in the form of an endless sheet, preferably a nonwoven and/or hydrophilic. Note that the article preform (60) may consist solely of the topsheet, whereby other components of the hygiene article, e.g. back sheet or absorbent core, can be attached in a later attachment process, preferably finally leading to a continuous production of longitudinally attached hygiene articles, which can be cut into separate hygiene articles.

The invention claimed is:

1. An absorbent hygiene article suitable to be worn around the waist of a wearer, the article comprising:
    a front region, a back region and a crotch region located longitudinally in between the front region and the back region;
    a liquid impermeable backsheet on a garment-facing side of the article, a liquid permeable topsheet on the body-facing side of the article and an absorbent core therebetween, the absorbent core substantially located in the crotch region;
    a leakage barrier comprising a pair of leg cuffs arranged longitudinally on the body-facing side of the article from the front region to the back region across the crotch region, a first leg cuff of said pair of leg cuffs being arranged near a first leg-hole-defining-edge of the article and a second leg cuff of said pair of leg cuffs being arranged near a second leg-hole-defining-edge of the article,
    each of the leg cuffs comprising a front end edge located in the front region, a back end edge located in the back region, a longitudinal proximal edge near a leg-hole-defining-edge of the article and attached to the topsheet, and a longitudinal distal edge substantially unattached for allowing the corresponding leg cuff to be lifted over the topsheet to create a longitudinal upstanding barrier,
    wherein each of the leg cuffs comprises one or more elastic members, the elastic members being arranged longitudinally near the distal edge of the leg cuff,
    wherein the leakage barrier further comprises:
        a front barrier located in the front region, the front barrier comprising a first front barrier edge attached to the first leg cuff near the distal edge of the first leg cuff, the front barrier comprising a second front barrier edge attached to the second leg cuff near the distal edge of the second leg cuff, the front barrier comprising a front barrier waist edge attached to the topsheet near a front waist edge of the article and the front barrier comprising a front barrier internal edge substantially unattached for allowing the front barrier to be lifted over the topsheet when the distal edges of the leg cuffs are also lifted over the topsheet, to create a transverse upstanding barrier in the front region of the article; and/or
        a back barrier located in the back region, the back barrier comprising a first back barrier edge attached to the first leg cuff near the distal edge of the first leg cuff, the back barrier comprising a second back barrier edge attached to the second leg cuff near the distal edge of the second leg cuff, the back barrier comprising a back barrier waist edge attached to the topsheet near a back waist edge of the article and the back barrier comprising a back barrier internal edge substantially unattached for allowing the back barrier to be lifted over the topsheet when the distal edges of the leg cuffs are also lifted over the topsheet, to create a transverse upstanding barrier in the back region of the article,
    characterized in that the front barrier and/or the back barrier comprises a liquid-impermeable nonwoven sheet comprising a weight of at most 18 gsm and in that the elastic members of the leg cuffs do not overlap with the front barrier and/or the back barrier, and
    wherein the front barrier and/or the back barrier does not comprise an elastic member.

2. The absorbent hygiene article according to claim 1, wherein the nonwoven sheet of the front barrier and/or of the back barrier comprises a weight of at most 15 gsm.

3. The absorbent hygiene article according to claim 1, wherein the leakage barrier is attached to the topsheet along or near to the longitudinal proximal edges of the leg cuffs by a longitudinal glue attachment zone and by a heat-sealed attachment zone which is located adjacent to the longitudinal glue attachment zone.

4. The absorbent hygiene article according to claim 1, wherein the elastic members are wrapped within folds near the distal edges of the leg cuffs, and whereby said elastic members are at least partly attached to the leg cuffs.

5. The absorbent hygiene article according to claim 4, whereby said elastic members are at least partly attached to the leg cuffs by glue.

6. The absorbent hygiene article according to claim 4, whereby said elastic members are attached to the leg cuffs along a full length of the elastic members.

7. The absorbent hygiene article according to claim 1, wherein the front barrier waist edge is attached to the topsheet near the front waist edge of the article via a transverse gluing zone and whereby the front barrier is furthermore attached to the topsheet at the first front barrier edge and/or at the second front barrier edge via a first and/or second heat-sealed attachment path, and/or wherein the back barrier waist edge is attached to the topsheet near the back waist edge of the article via a transverse gluing zone and whereby the back barrier is furthermore attached to the topsheet at the first back barrier edge and/or at the second back barrier edge via a third and/or fourth heat-sealed attachment path.

8. The absorbent hygiene article according to claim 1, wherein the nonwoven sheet of the front barrier and/or of the back barrier comprises a weight of at most 12 gsm.

9. The absorbent hygiene article according to claim 1, wherein the absorbent hygiene article is a diaper, diaper pants or incontinence diaper.

10. A method of manufacturing an absorbent hygiene article according to claim 1, comprising the steps of:
(1) providing an article preform comprising a front region, a back region and a crotch region located longitudinally in between the front region and the back region, the article preform further comprising a liquid impermeable backsheet on a garment-facing side of the article, a liquid permeable topsheet on the body-facing side of the article and an absorbent core therebetween, the absorbent core substantially located in the crotch region;
(2) providing a leakage barrier comprising a pair of leg cuffs, each of the leg cuffs comprising a front end edge, a back end edge, a longitudinal proximal edge and a longitudinal distal edge,
wherein each of the leg cuffs comprises one or more elastic members, the elastic members being arranged longitudinally near the distal edge of the leg cuff,
wherein the leakage barrier further comprises:
a front barrier comprising a first front barrier edge attached to the first leg cuff near the distal edge of the first leg cuff, the front barrier comprising a second front barrier edge attached to the second leg cuff near the distal edge of the second leg cuff, the front barrier comprising a front barrier waist edge and the front barrier comprising a front barrier internal edge; and/or
a back barrier comprising a first back barrier edge attached to the first leg cuff near the distal edge of the first leg cuff, the back barrier comprising a second back barrier edge attached to the second leg cuff near the distal edge of the second leg cuff, the back barrier comprising a back barrier waist edge and the back barrier comprising a back barrier internal edge,
(3) attaching the leakage barrier to the body-facing side of the article preform,
characterized in that the front barrier and/or the back barrier comprises a liquid-impermeable nonwoven sheet comprising a weight of at most 18 gsm and in that the elastic members of the leg cuffs do not overlap with the front barrier and/or the back barrier.

11. Method according to claim 10, wherein the front barrier comprises a front barrier waist edge, a first and a second front barrier edge, the back barrier comprises a back barrier waist edge, a first and a second back barrier edge, and the topsheet comprises a front waist edge and a back waist edge;

wherein the step (3) of attaching the leakage barrier to the body-facing side of the article preform comprises:
attaching the front barrier waist edge to the topsheet near the front waist edge of the article preform via a transverse gluing zone and furthermore attaching the front barrier to the topsheet at the first front barrier edge and/or at the second front barrier edge via a first and/or second heat-sealed attachment path, and/or
attaching the back barrier waist edge to the topsheet near the back waist edge of the article preform via a transverse gluing zone and furthermore attaching the back barrier to the topsheet at the first back barrier edge and/or at the second back barrier edge via a third and/or fourth heat-sealed attachment path.

12. Method according to claim 10, wherein the first back barrier edge is attached to the first leg cuff and/or the first front barrier edge is attached to the first leg cuff by heat-sealing.

13. Method according to claim 12, wherein at least one leg cuff comprises at least one elastic member which is wrapped within a fold near the distal edge of the leg cuff, whereby the heat-sealing of the first back barrier edge to the first leg cuff and/or the first front barrier edge to the first leg cuff is performed along a heat-sealing path which stretches along a full length of said leg cuff such that the elastic member in said leg cuff is located between the heat-sealing path and the distal edge of said leg cuff.

14. Method according to the preceding claim 13, wherein the at least one elastic member is wrapped in a distal edge of the unwrapped fold of the leg cuff by applying glue to said at least one elastic member and/or by applying glue to said distal edge of the unwrapped fold of the leg cuff, and subsequently folding said unwrapped fold of the leg cuff around said at least one elastic member.

15. A leakage barrier for an absorbent hygiene article, which article comprises a front region, a back region and a crotch region located longitudinally in between the front region and the back region, and a liquid impermeable backsheet on a garment-facing side of the article, a liquid permeable topsheet on the body-facing side of the article and an absorbent core therebetween, the absorbent core substantially located in the crotch region,
said leakage barrier comprising a pair of leg cuffs arranged essentially parallel along a longitudinal direction, each of the leg cuffs comprising a front end edge and a back end edge longitudinally opposite of said first longitudinal end, each of the leg cuffs further comprising a longitudinal proximal edge and a longitudinal distal edge between the front end edge and the back end edge, wherein each of the leg cuffs comprises one or more elastic members, the elastic members being arranged longitudinally near the distal edge of the leg cuff, wherein the leakage barrier further comprises:
a front barrier comprising a first front barrier edge attached to the first leg cuff near the distal edge of the first leg cuff and located near the front end edge, the front barrier comprising a second front barrier edge attached to the second leg cuff near the distal edge of the second leg cuff and located near the front end edge, the front barrier comprising a front barrier waist edge and a front barrier internal edge between the first front barrier edge and the second front barrier edge; and/or a back barrier comprising a first back barrier edge attached to the first leg cuff near the distal edge of the first leg cuff and located near the back end edge, the back barrier comprising a second back barrier edge attached to the second leg cuff near the distal edge of the second leg cuff and located near the back end edge, the back barrier comprising a back barrier waist edge and a back barrier internal edge between the first back barrier edge and the second back barrier edge, characterized in that the front barrier and/or the back barrier comprises a liquid-impermeable nonwoven sheet comprising a weight of at most 18 gsm and in that the elastic members of the leg cuffs do not overlap with the front barrier and/or the back barrier, and wherein the front barrier and/or the back barrier does not comprise an elastic member.

16. Method of manufacturing a leakage barrier as described in the preceding claim 15, comprising the steps of:

attaching the first front barrier edge to the first leg cuff near the distal edge of the first leg cuff at or near the front end edge and attaching the second front barrier edge to the second leg cuff near the distal edge of the second leg cuff at or near the front end edge, and/or attaching the first back barrier edge to the first leg cuff near the distal edge of the first leg cuff at or near the back end edge and attaching the second back barrier edge to the second leg cuff near the distal edge of the second leg cuff at or near the back end edge.

17. Method according to claim 16, wherein the first back barrier edge and second back barrier edge are attached by heat-sealing, and wherein at least one leg cuff comprises at least one elastic member which is wrapped within a fold near the distal edge of the leg cuff, whereby the heat-sealing is performed along a heat-sealing path which stretches along a full length of said leg cuff such that the elastic member in said leg cuff is located between the heat-sealing path and the distal edge of said leg cuff.

* * * * *